United States Patent
Eder et al.

(10) Patent No.: US 7,019,028 B2
(45) Date of Patent: Mar. 28, 2006

(54) ENDIANDRIC ACID H AND ITS DERIVATIVES, PROCESS FOR THEIR PREPARATION AND USE THEREOF

(75) Inventors: Claudia Eder, Hofheim (DE); Herbert Kogler, Glashutten (DE); Sabine Haag-Richter, Frankfurt (DE)

(73) Assignees: Aventis Pharma Deutschland GmbH, Frankfurt am Main (DE); Aventis Pharmaceuticals Inc., Bridgwater, NJ (US)

( * ) Notice: Subject to any disclaimer, the term of this patent is extended or adjusted under 35 U.S.C. 154(b) by 13 days.

(21) Appl. No.: 10/627,850

(22) Filed: Jul. 25, 2003

(65) Prior Publication Data

US 2004/0138313 A1 Jul. 15, 2004

Related U.S. Application Data

(60) Provisional application No. 60/438,283, filed on Jan. 6, 2003.

(30) Foreign Application Priority Data

Aug. 2, 2002 (DE) ................. 102 35 624

(51) Int. Cl.
- *A61K 31/36* (2006.01)
- *C07D 317/44* (2006.01)

(52) U.S. Cl. .............. 514/464; 514/465; 514/466; 549/440; 549/441; 549/444; 549/445; 549/447

(58) Field of Classification Search ............... 514/464, 514/465, 466; 549/440, 441, 444, 445, 447
See application file for complete search history.

(56) References Cited

OTHER PUBLICATIONS

Anuradha Ray et al., Th2 Cells and GATA-3 in Asthma: new insights into the Regulation of Airway Inflammation, The Journal of Clinical Investigation (1999, pp. 985-993, vol. 104, No. 8).

I-Cheng Ho et al., c-maf Promotes T Helper Cell Type 2 (Th2) and Attenuates Th1 Differentiation by Both Interleukin 4-Dependent and -independent Mechanisms, J. Exp. Med. (1998, pp. 1859-1866, vol. 188, No. 10).

James E. Banfield et al., Constituents of Some Species of Beilschmiedia and Endiandra (Lauraceae): New Endiandric Acid and Benzopyran Derivatives Isolated from B. Oligandra, Aust. J. Chem. (1981, pp. 1655-1667, vol. 34).

James I. Kim et al., The Transcription Factor c-Maf Controls the Production of Interleukin-4 but Not Other Th2 Cytokines, Immunity, (1999, pp. 745-751, vol. 10).

(Continued)

*Primary Examiner*—Rita Desai
(74) *Attorney, Agent, or Firm*—Joseph Strupczewski

(57) ABSTRACT

The invention relates to compounds of the formula (I)

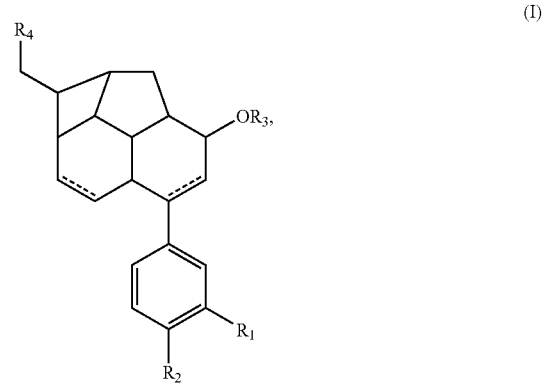

process for their preparation starting from the plant *Beilschmiedia fulva*, PLA 101037, and the use thereof for producing a medicament, in particular for the treatment of allergic disorders, of asthmatic disorders, of inflammatory concomitant symptoms of asthma and/or of diseases which can be treated by inhibiting c-maf and NFAT.

8 Claims, No Drawings

OTHER PUBLICATIONS

K. C. Nicolaou et al., The Endiandric Acid Cascade. Electrocyclizations in Organic Synthesis. 1. Stepwise, Stereocontrolled Total Synthesis of Endiandric Acids A and B, J. Am. Chem. Soc. (1982, pp. 5555-5557, vol. 104).

K. C. Nicolaou et al., The Endiandric Acid Cascade. Electrocyclizations in Organic Synthesis. 4. "Biomimetic" Approach to Endiandric Acids A-G. Total Synthesis and Thermal Studies, J. Am. Chem. Soc. (1982, pp. 5560-5562, vol. 104).

Paul S. Foster et al., Interleukin-5 and Eosinophils as Therapeutic Targets for Asthma, Trends in Molecular Medicine ( 2002, pp. 162-167, vol. 8, No. 4).

Wickramasinghe M. Bandaranayake et al., Constituents of Endiandra Species. I+ Endiandric Acid, a Novel Carboxylic Acid from Endiandra introrsa (Lauraceae), and a Derived Lactone, Aust. J. Chem. (1981, pp. 1655-1657, vol. 34).

ENDIANDRIC ACID H AND ITS DERIVATIVES, PROCESS FOR THEIR PREPARATION AND USE THEREOF

This application claims the benefit of U.S. Provisional Application No. 60/438,283 filed Jan. 6, 2003, and right of priority from German Patent Application No. 10235624.6, filed Aug. 2, 2002.

Asthma is a disorder of the immune system which is manifested for example as bronchial asthma in the form of episodes of acutely occurring shortness of breath with expiratory ventilation obstruction. The only medicaments available to date for treating asthma are those which alleviate the symptoms, but none which intervene to inhibit the mechanism responsible for the expression of mediators of inflammation. These mediators of inflammation, especially the cytokines interleukin-4 (IL-4), interleukin-13 (IL-13) and interleukin-5 (IL-5) are overexpressed in the asthmatic disorder and are responsible for inflammation, eosinophilia, mucus formation and bronchial hyperreactivity, which maintain the disease. The expression of these cytokines is increased in the lungs of asthmatics (Ray & Cohn, J. Clin. Invest. 1999, 104(8), 985–993). Studies with transgenic animals showed that a knockout of the IL-4 gene reduces the allergic inflammatory reactions. Kim et al. (Immunity 1999, 10, 745) has shown that the transcription factor of c-maf is responsible for the tissue-specific expression of IL-4 in a subclass of T-helper cells and thus for allergic inflammatory reactions. c-maf belongs to the Maf family, a family of leucine-containing zipper proteins, which is involved in the regulation of the expression of a whole series of genes. In TH2 cells, a subgroup of CD4+ helper cells, c-maf brings about, in synergy with NFAT (nuclear factor of activated T cells), a transactivation of the IL-4 promoter, which in turn leads to an increase in the cytokine concentration.

An inhibitor of c-maf ought therefore to reduce the cytokine concentration, resulting in a lower IL-4 level, which leads to a reduced IgE (immunoglobulin E) concentration because IL-4 is crucial for the stimulation of B cells to produce IgE. A reduction in IgE in turn would result in a reduced mast cell degranulation and a reduced release of histamine, serotonin and other inflammatory factors. On the other hand, Ho et al. (J. Exp. Med., 1998,10, 1859–1866) describe regulation of the concentration of the TH2 phenotype by IL-4 in an autocrine pathway. A reduction in the IL-4 level therefore results in a reduction in this T-cell type, which in turn shifts the equilibrium between TH1 and TH2 in the direction of TH1. This would further reduce the IL-4 concentration and would have the additional advantage of reducing the IL-5 or IL-13 production, which would result in a reduction in the eosinophilia, mucus formation and bronchial hyperreactivity.

Genes selectively expressed in TH2 cells are therefore preferred targets for a therapeutic application for selectively influencing the inflammatory component in asthma and allergy.

In this connection, IL-4 and IL-5 antibodies are currently being tested in clinical study (Foster et al., Trends Mol. Med., 2002, 8,162). It is expected that selective therapeutic agents will replace the widespread therapy with glucocorticoids, which has to date represented the only possibility for controlling the inflammatory reactions in asthma.

A tetracyclic compound of the formula

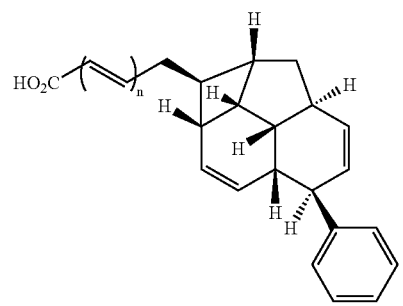

in which n is 0 is referred to as endiandric acid A, and in which n is 1 as endiandric acid B. The compounds can be obtained from extracts of the Lauraceae family of plants, specifically of the genera *Endiandra* and *Beilschmiedia* (Bandaranayake et al., Aust. J. Chem., 1981, 34, 1655–67; Banfield et al., Aust. J. Chem., 1994, 47, 587–607).

Bandaranayake et al. describe the dihydro and tetrahydro derivatives of endiandric acid A, obtainable by partial or complete reaction with hydrogen in the presence of Pd/C.

Banfield et al. describe endiandric acid A substituted on the phenyl radical by a methylenedioxy group.

Also known are derivatives of endiandric acid A and B in which the acid group is refunctionalized, for example as $CH_2OSiPh_2t\text{-}Bu$, $CH_2Br$, $CH_2CN$, esterified to $CO_2CH_3$, or reduced to the aldehyde CHO or to the alcohol $CH_2OH$ (Nicolaou et al., J. Am. Chem. Soc., 1982, 104, 5555–5557 and 5560–5562).

Endiandric acid derivatives in which the double bond in the ring adjacent to the phenyl ring is in conjugation with the phenyl ring have not previously been disclosed. Bandaranayake et al. describe the failure of corresponding isomerization attempts.

The biological effect of endiandric acid derivatives has not previously been investigated.

It is an object of the present invention to provide novel endiandric acid derivatives.

It has been found, surprisingly, that the African plant *Beilschmiedia fulva* is able to produce highly active novel compounds which are active as c-maf inhibitors.

The present invention therefore relates to a compound of the formula (I)

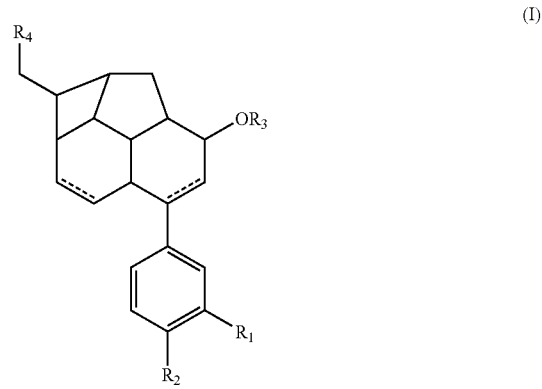

where
R$_1$ and R$_2$ are, independently of one another,
0.0 H or
1.0 a —O—C$_1$–C$_6$-alkyl, —O—C$_2$–C$_6$-alkenyl, —O—C$_2$–C$_6$-alkynyl or —O—C$_6$–C$_{10}$-aryl group, in which alkyl, alkenyl and alkynyl are straight-chain or branched, and in which the alkyl, alkenyl and alkynyl groups are optionally mono- or disubstituted by:
2.1 —OH,
2.2 =O,
2.3 —O—C$_1$–C$_6$-alkyl in which alkyl is straight-chain or branched,
2.4 —O—C$_2$–C$_6$-alkenyl in which alkenyl is straight-chain or branched,
2.5 —C$_6$–C$_{10}$-aryl,
2.6 —NH—C$_1$–C$_6$-alkyl in which alkyl is straight-chain or branched,
2.7 —NH—C$_2$–C$_6$-alkenyl in which alkenyl is straight-chain or branched,
2.8 —NH$_2$ or
2.9 halogen,
and in which the aryl groups are optionally mono- or disubstituted by substituents 2.1 or 2.3 to 2.9,
in which the substituents 2.3, 2.4, 2.6 and 2.7 may be further substituted by —CN, -amide or -oxime functions, and 2.5 may be further substituted by —CN or amide functions
or
R$_1$ and R$_2$ together form a ring, in which case R$_1$ and R$_2$ are a group —O—[(C$_1$–C$_6$)-alkylene]-O—,
R$_3$ is
1.0 H or
2.0 a C$_1$–C$_6$-alkyl, C$_2$–C$_6$-alkenyl, C$_2$–C$_6$-alkynyl or C$_6$–C$_{10}$-aryl group, in which alkyl, alkenyl and alkynyl are straight-chain or branched, and in which the alkyl, alkenyl and alkynyl groups are optionally mono- or disubstituted by:
2.1 —OH,
2.2 =O,
2.3 —O—C$_1$–C$_6$-alkyl in which alkyl is straight-chain or branched,
2.4 —O—C$_2$–C$_6$-alkenyl in which alkenyl is straight-chain or branched,
2.5 —C$_6$–C$_{10}$-aryl,
2.6 —NH—C$_1$–C$_6$-alkyl in which alkyl is straight-chain or branched,
2.7 —NH—C$_2$–C$_6$-alkenyl in which alkenyl is straight-chain or branched,
2.8 —NH$_2$ or
2.9 halogen,
and in which the aryl groups are optionally mono- or disubstituted by substituents 2.1 or 2.3 to 2.9,
in which the substituents 2.3, 2.4, 2.6 and 2.7 may be further substituted by —CN, -amide or -oxime functions, and 2.5 may be further substituted by —CN or amide functions, and
R$_4$ is
CO$_2$R$_3$, CO$_2$NHR$_3$, CHO, CH$_2$OR$_3$, CH$_2$OSi(R$_3$)$_3$, CH$_2$Br, CH$_2$CN, where R$_3$ is as defined above, or a stereoisomeric form of the compound of the formula (I) or a physiologically tolerated salt of the compound of the formula (I) or a salt of a stereoisomeric form of the compound of the formula (I).

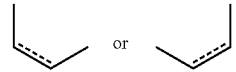

means independently of one another a single bond or a double bond.

The invention preferably relates to a compound of the formula (II)

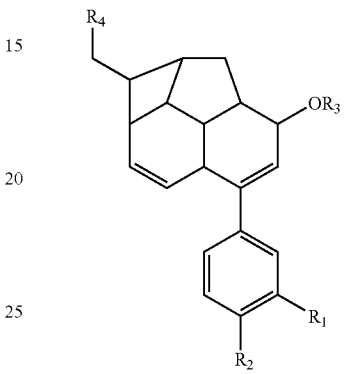

where the radicals R$_1$ to R$_4$ are as defined above.

As used herein, "C$_1$–C$_6$-Alkyl" is a straight-chain or branched alkyl having 1 to 6 carbon atoms, preferably having 1 to 4 carbon atoms, e.g. methyl, ethyl, i-propyl, tert-butyl and hexyl.

As used herein, "C$_2$–C$_6$-Alkenyl" is a straight-chain or branched alkenyl having 2 to 6 carbon atoms, which is mono-, di- or triunsaturated, e.g. allyl, crotyl, 1-propenyl, penta-1,3-dienyl and pentenyl.

As used herein, "C$_2$–C$_6$-Alkynyl" is a straight-chain or branched alkynyl having 2 to 6 carbon atoms, which is mono- or diunsaturated, e.g. propynyl, butynyl and pentynyl.

As used herein, "C$_6$–C$_{10}$-Aryl" is an aryl group having 6 to 10 carbon atoms, e.g. phenyl, benzyl or 1- or 2-naphthyl, which may also be substituted, for example by halogen such as chlorine, bromine, fluorine, by alkyl having 1–4 carbon atoms, preferably methyl, by hydroxyl, by alkoxy having 1–4 carbon atoms, in particular methoxy, or by trifluoromethyl.

As used herein, "C$_1$–C$_6$-Alkylene" means an alkylene group having 1 to 6 carbon atoms, preferably having 1 to 4 carbon atoms, e.g. methylene, ethylene, i-propylene, tert-butylene and hexylene.

As used herein, "treat" or "treating" means any treatment, including but not limited to, alleviating symptoms, eliminating the causation of the symptoms either on a temporary or permanent basis, or to preventing or slowing the appearance of symptoms and progression of the named disease, disorder or condition.

R$_1$ and R$_2$ are preferably H or a group —O—[(C$_1$–C$_6$)-alkyl]-O—, particularly preferably —O—CH$_2$—O—.

R$_3$ is preferably H.

R$_4$ is preferably COOR$_3$, where R$_3$ preferably H.

The invention particularly preferred relates to a compound of the formula (III)

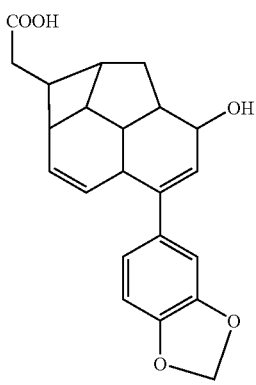

(III)

The invention particularly most preferred relates to a compound of the formula (IV), which is referred to hereinafter as endiandric acid H:

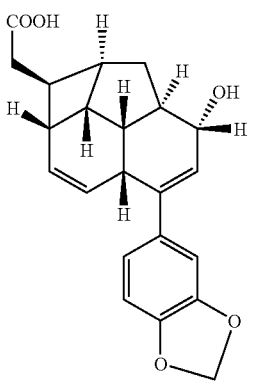

(IV)

The compounds of the invention of the formula (I) contain a tetracyclic ring system with a phenyl radical which, in contrast to the compounds described previously, is in conjugation with one of the two double bonds in the tetracyclic ring system, and have an additional hydroxyl group. Because of their different chemical structure, the compounds of the formula (I) have novel physicochemical, biological and pharmacological properties.

The invention further relates to a compound obtainable from the plant *Beilschmiedia fulva*, PLA 101037, or cell cultures of the plant *Beilschmiedia fulva*, PLA 101037, characterized by the molecular formula $C_{22}H_{21}O_5$, by the $^1$H-NMR chemical shifts δ=1.733, 1.801, 1.209, 1.851, 1.946, 2.339, 2.354, 2.400 2.440, 2.765, 3.351, 4.000, 5.207, 5.593, 5.845, 6.00, 6.01, 6.873, 6.908, 6.995 and by the $^{13}$C-NMR chemical shifts δ=33.62, 33.76, 34.82, 34.99, 40.32, 40.61, 40.69, 40.90, 44.02, 71.96, 100.92, 106.66, 108.10, 119.86, 126.33, 127.59, 131.41, 133.76, 140.15, 146.48, 147.51 173.47.

The invention further relates to a process for preparing the compound of the formula (I), which comprises
1. extracting the plant *Beilschmiedia fulva*, PLA 101037, or cell cultures of the plant *Beilschmiedia fulva*, PLA 101037, under suitable conditions,
2. isolating the compound of the formula (IV), and
3. where appropriate derivatizing to a compound of the formula (I) and/or reacting to give a physiologically tolerated salt of the compound of the formula (I).

The invention further relates to a process for preparing a compound of the formula (IV), which comprises
1. extracting the plant *Beilschmiedia fulva*, PLA 101037, or cell cultures of the plant *Beilschmiedia fulva*, PLA 101037, under suitable conditions,
2. isolating the compound of the formula (IV), and
3. where appropriate reacting to give a physiologically tolerated salt of the compound of the formula (IV).

For the extraction of the compound of the formula (IV) from the plant *Beilschmiedia fulva* or one of its variants or mutants, the latter is initially cultivated under suitable conditions until endiandric acid H of the formula (IV) accumulates in the plant material. The plant *Beilschmiedia fulva*, its mutants and/or variants is preferably cultivated on suitable soils in a tropical or subtropical climate. Production of the plants is particularly preferably carried out under tropical conditions, for example at a temperature between 18 and 35° C. and at a humidity of greater than or equal to 70%, preferably of 70–90%.

To extract the compound of the formula (IV) from living cells of the plant *Beilschmiedia fulva*, the latter are initially transferred into a suitable nutrient solution and cultivated until the compound of the invention of the formula (IV) accumulates in the medium. The cell cultures are preferably set up as callus cultures. The nutrient media consist, besides minerals and vitamins, also of at least one carbon source, for example sucrose, and at least one nitrogen source, such as, for example, a nitrate or ammonium salt.

*Beilschmiedia fulva* is a tree from the Lauraceae family. The Lauraceae family includes many evergreen tropical spice plants and useful plants. The geographical range of the Lauraceae covers the entire tropics: the sample of the plant *Beilschmiedia fulva*, PLA 101037, was collected in Gabon, specifically in the area around la Makandé in the region of the canopy of the rainforest. The sample was collected in the direct vicinity of the Mankandé Research Field Station (coordinates 0° 40' 860" S-11° 54' 750" E). *Beilschmiedia fulva* is a tree which may reach a height of 30 m and thus forms part of the canopy region of the rainforest. The leaves are bluish green, and the fruit is red. The trunk is cylindrical at the base and is sparsely covered with bark of brittle consistency and has a brownish-reddish color. The bark layer is about 4–5 mm thick and has a characteristic odor.

It is also possible to use other species from the genus *Beilschmiedia*, or else plants of the same species derived from a different site, to isolate endiandric acid H. The content of endiandric acid H may vary depending on the site conditions such as, for example soil characteristics, temperature, moisture, light incidence.

The process of the invention can be employed for extraction and isolation in a wide range of plant material to be extracted, for example on the laboratory scale (100 g to 1 kg of dried plant material) up to the industrial scale (100 to >1000 kg).

The plant *Beilschmiedia fulva* can be cultivated outside or, preferably, in a greenhouse.

An alternative possibility is to employ cell cultures of *Beilschmiedia fulva* plants to produce the compounds of the invention. This is normally done by cultivation in a plurality of stages, i.e. firstly one or more precultures are produced in a suitable liquid medium and can then be used to inoculate the main culture. The starting material is usually callus cultures. It is possible by choosing suitable bioreactors for growing the plant cell culture to achieve optimal mixing and aeration of the culture without the plant cells being exposed to excessive shear forces, and thus optimal cell growth and metabolite production. It is possible to employ for example airlift or bubble column reactors, and paddle or propeller stirrers for mixing the cultures. The cells may grow as single cells or branched or unbranched cell aggregates or chains. Metabolite production can be induced by stimulation with exogenous factors, e.g. heavy metal salts or plant elicitors.

Product formation in the plant cell culture can be monitored by means of the pH of the cultures and by chromatographic methods such as, for example, thin layer chromatography, HPLC or testing the biological activity. Endiandric acid H of the formula (IV) may be present, besides the bark, also in other parts of the plant.

The endiandric acid H of the invention of the formula (IV) is isolated and purified from the plant or the culture medium by known methods which take account of the chemical, physical and biological properties of the natural products. HPLC can be used to assay the concentration of the compounds of the invention in the starting material or in the individual stages of isolation, it being expedient to compare the amount of substance formed with a calibration solution.

To isolate the endiandric acid H of the invention of the formula (IV), the *Beilschmiedia fulva* plant is harvested, initially collecting the leaves, stems, wood, the bark or roots and separating according to parts of the plant, while still in the fresh state or dry, and then extracting from the plant material with an organic solvent which contains water where appropriate. The compounds of the invention are preferably isolated by extracting the bark.

The extracts are combined, diluted with water and extracted with a suitable, water-immiscible organic solvent, for example with n-butanol. The organic phase which has subsequently been separated off is concentrated where appropriate in vacuo. Fats can be removed from the required product by diluting the concentrate with a nonpolar solvent in which the endiandric acid H derivative according to the invention is very slightly soluble, such as, for example, with hexane, petroleum ether, diethyl ether. This entails precipitation of the endiandric acid H, and the lipophilic impurities remain dissolved and are removed by conventional solid/liquid phase separations. The precipitate containing the endiandric acid H is lyophilized. The lyophilizate is purified further.

Further purification of endiandric acid H takes place by chromatography on suitable materials, preferably, for example, on molecular sieves, on normal phase supports such as, for example, silica gel, alumina, on ion exchangers or on adsorber resins, or on reverse phases (reversed phase, RP). The endiandric acid H is removed by means of this chromatography. The chromatography of the endiandric acid H takes place with buffered aqueous solutions or mixtures of aqueous and organic solutions.

Mixtures of aqueous and organic solutions mean all water-miscible organic solvents, preferably methanol, 2-propanol and acetonitrile, in a concentration of from 10 to 90% of solvent, preferably 15 to 60% of solvent, or else all buffered aqueous solutions which are miscible with organic solvents.

The endiandric acid H is removed with the aid of reversed phase chromatography, for example on MCI® (adsorber resin from Mitsubishi, Japan) or Amberlite XAD® (TOSO-HAAS), on other hydrophobic materials such as, for example, on RP-8 or RP-18 phases or on polyamides. Separation is additionally possible with the aid of gel chromatography or normal phase chromatography, for example on silica gel or alumina.

The chromatography of endiandric acid H takes place with buffered or acidified aqueous solutions or mixtures of aqueous solutions with alcohols or other water-miscible organic solvents. Propanol and acetonitrile is preferably used as organic solvent.

Buffered or acidified aqueous solutions mean, for example, water, phosphate buffer, citrate buffer, ammonium acetate in a concentration of from 1 mM to 0.5 M, preferably 10 mM, and formic acid, acetic acid, trifluoroacetic acid or all commercially available acids known to the skilled worker, preferably in a concentration of from 0.01 to 3%.

Chromatography is carried out with a gradient which starts with 100% aqueous buffer and finishes with 100% solvent, preferably running a linear gradient from 10 to 60% 2-propanol or acetonitrile.

The gel chromatography is carried out on polyacrylamide or copolymer gels such as, for example, Biogel-P 2® (from Biorad), Fractogel TSK HW 40® (from Merck, Germany or Toso Haas, USA) or on Sephadex® (Pharmacia, Uppsala, Sweden).

The sequence of the aforementioned chromatographies may be reversed.

A further purification step for the compounds of the invention is crystallization. For example, endiandric acid H of the formula (IV) crystallizes from organic solvents and from mixtures of water with organic solvents. The crystallization is carried out in a manner known per se for example by concentrating or cooling saturated solutions.

Endiandric acid H of the formula (IV) is stable in the solid state and in solutions in the pH range between 3 and 8, in particular 4 and 6.

The compound of the formula (I) can be derivatized by methods known per se (J. March, Advanced Organic Synthesis, 4th Edition, John Wiley & sons., 1992). For example, the carboxyl function can be esterified or reduced to the primary alcohol, or it can be converted into an amide. Carbonyl groups can be reduced with metal hydrides such as aluminum hydrides or boron hydrides. Reduction to the saturated compounds can be achieved for example with hydrogen in the presence of suitable catalysts. The hydroxyl function can be esterified.

Compounds of the formula (I) can be converted into their physiologically tolerated salts by methods known to the skilled worker.

Physiologically tolerated salts of compounds of the formula (I) mean both their organic and inorganic salts as described in Remington's Pharmaceutical Sciences (17th edition, page 1418 (1985)). Because of the physical and chemical stability and the solubility, sodium, potassium, calcium and ammonium salts are preferred, inter alia, for acidic groups. Preferred for basic groups are, inter alia, salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid.

The present invention includes all stereoisomeric forms of the compounds of the formula (I). All possible enantiomers and diastereomers, as well as mixtures of two or more stereoisomeric forms, for example mixtures of enantiomers and/or diastereomers, in all ratios, belong to the invention. The invention relates to enantiomers in enantiopure form, both as levorotatory and as dextrorotatory antipodes, R and S configurations, in the form of racemates and in the form of mixtures of the two enantiomers in all ratios. If a cis/trans isomerism exists, the invention relates both to the cis form and to the trans form and to mixtures of these forms in all ratios.

Because of the pharmacological properties, the compounds of the invention of the formula (I) are suitable for use as medicaments in human and/or veterinary medicine.

The invention therefore relates to a medicament having a content of at least one compound of the formula (I) and of one or more physiologically suitable excipients.

The medicaments of the invention are generally administered orally, locally or parenterally, but rectal use is also possible in principle. Examples of suitable solid or liquid pharmaceutical forms are granules, powders, tablets, coated tablets, (micro)-capsules, suppositories, syrups, emulsions, suspensions, aerosols, drops or injectable solutions in ampul form, and products with protracted release of active ingredient, in the production of which normally physiologically suitable aids such as carriers, disintegrants, binders, coating agents, swelling agents, glidants or lubricants, flavorings, sweeteners or solubilizers are used. Carriers or excipients which are frequently used and which may be mentioned are, for example, magnesium carbonate, titanium dioxide, lactose, mannitol and other sugars, talc, milk protein, gelatin, starch, vitamins, cellulose and its derivatives, animal or vegetable oils, polyethylene glycols and solvents such as, for example, sterile water, alcohols, glycerol and polyhydric alcohols.

It is possible where appropriate for the dosage units for oral administration to be microencapsulated so that delivery is delayed or extended over a longer period, such as, for example, by coating or embedding the active ingredient in particulate form in suitable polymers, waxes or the like.

The pharmaceutical products are preferably produced and administered in dosage units, with each unit containing as active ingredient a particular dose of at least one compound of the formula (I). In the case of solid dosage units such as tablets, capsules and suppositories, this dose may be up to 1 g, preferably about 0.1 to 200 mg, and in the case of injectable solutions in ampul form may be up to 1 g, preferably about 0.1 to 100 mg.

The daily dose to be administered depends on the body weight, age, sex and condition of the mammal. However, higher or lower daily doses may also be appropriate in some circumstances. Administration of the daily dose may take place both by a single administration in the form of a single dosage unit or else in a plurality of smaller dosage units and by multiple administration of divided doses at particular intervals.

The medicaments of the invention are produced by converting one or more compounds of the formula (I) with one or more physiologically suitable excipients in a suitable dosage form.

The invention further relates to the use of a compound of the formula (I) for producing a medicament, in particular for the treatment of allergic disorders, of asthmatic disorders, of inflammatory concomitant symptoms of asthma and/or of diseases which can be treated by inhibition of c-maf and NFAT.

The zipper protein c-maf represents the assay target. It plays an important part in the release of mediators of inflammation, especially IL-4, and thus in the manifestation of inflammatory symptoms in asthma and allergies. c-maf is thus an important therapeutic target molecule for asthma, especially if it has an allergic cause. The activity of c-maf is measured in the assay on the basis of the IL-4 transcription rate. Compounds which interfere with the binding of the two transcription factors c-maf and NFAT lead in this case to a reduced expression of luciferase (read-out) through suppression of the transcription of a human IL-4 promoter/luciferase construct.

The following examples are intended to explain the invention in more detail without wishing to restrict the scope of the invention in any way. Percentage data are based on weight. Mixing ratios of liquids are based on volume unless stated otherwise.

EXAMPLES

Example 1

Plant Production (Collection of the Seeds, Sowing, and Growing and Harvesting Conditions)

Seeds of *Beilschmiedia fulva* were collected after ripening and sown to cultivate the plants further in a greenhouse. The optimal temperature was about 28° C. with a humidity of 70–90%. The plants were cultivated for several months to years until the bark and other suitable parts of the plants were harvested.

Example 2

Preparation of a Primary Extract from *Beilschmiedia fulva*

Pieces of *Beilschmiedia fulva* bark were collected in the fresh state and then dried in air at about 40° C. After drying, 100 g of dry material were ground and extracted with 1 l of methanol at 40° C. for 8 h while stirring. After the extraction was complete, the plant residues were filtered off and the methanolic extract was concentrated almost to dryness in vacuo. The residue was resuspended again in a little water and then freeze dried. The primary extract produced in this way could be stored at +4° C. to −20° C. or be used for further isolation as in example 3. To assay the biological activity, tannins and other strongly hydrophilic or lipophilic interfering substances were removed from the primary extract by chromatography on polyamide and on polystyrene adsorber resin.

Example 3

Isolation of Endiandric Acid H from the Plant *Beilschmiedia fulva*

100 g of dried pieces of *Beilschmiedia fulva* bark are harvested as in example 2, comminuted in a mill, stirred with 1 l of methanol for 16 hours and then filtered. The active ingredient-containing methanolic solution is concentrated in vacuo; the dry matter amounts to 7.0 g. The concentrate is loaded onto a prepared glass column (BPG 100, 4 l internal volume, from Pharmacia Biotech) which is packed with about 0.5 l of MCI gel® CHP-20P material (adsorber resin from Mitsubishi Chemicals, Japan). A gradient from 100% water to 100% acetonitrile is used for elution. The column flow-through (50 ml per minute) is collected in fractions (50 ml each), and fractions active in the bioassay (fraction 18–21) are combined. Concentration in vacuo and freeze drying afford 102 mg of pale brown powder.

Example 4

Purification of Endiandric Acid H by Reversed Phase HPLC

The 102 mg of the powder obtained in example 3 were loaded onto a LUNA® 10µ C18 (2) column (size: 21.2 mm×240 mm, from Phenomenex, Germany) and chromatographed with a gradient from 3% to 6% acetonitrile in 0.1% ammonium acetate/water over 60 minutes. The flow-through of eluent amounts to 33 m/min, and the size of the fractions is 33 ml. Endiandric acid H is present in fractions 24 and 25. Lyophilization of said fractions affords 3.7 mg of pure substance (purity>95%).

Example 5

Characterization of Endiandric Acid H

Appearance: white substance which is soluble in polar organic solvents, but only slightly soluble in water.

UV maxima (in water/acetonitrile): 206, 262, 296.

The following was found by high-resolution mass spectrometry for $(M+H)^+$: 365.1392 amu. This corresponds to a molecular formula of endiandric acid H of $C_{22}H_{21}O_5$.

Electron spray ionization (ESI, positive) results by MS/MS fragmentation in the following ions: 349 amu ($M+H-H_2O$) to 331 amu ($-H_2O$), 303 amu ($-CH_2O_2$), 289 amu ($-C_2H_4O_2$).

Electron spray ionization (ESI, negative) results by MS/MS fragmentation in the following ions: 365 amu $(M-H)^-$ to 321 amu ($-CO_2$), 267 amu ($-C_5H_6O_2$) 227 amu ($-C_8H_{10}O_2$), 215 amu ($-C_9H_{10}O_2$) and smaller fragments.

TABLE 1

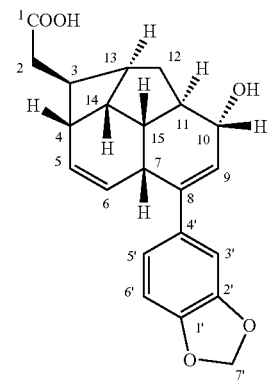

NMR chemical shifts and coupling constants of endiandric acid H, DMSO, 303 K.

| Pos. | δ ($^{13}C$) | m ($^{13}C$) | δ ($^1H$) | m ($^1H$) | $^nJ$CH | $^nJ$HH$^{(J/Hz)}$ |
|---|---|---|---|---|---|---|
| 1 | 173.47 | s | — | — | 2.44, 2.40 | — |
| 2 | 40.69 | t | 2.440, 2.400 | dd dd | 1.73, 2.35 | 1.73 (8.2), 2.40 (12.2) 1.73 (7.7), 2.44 (12.2) |
| 3 | 40.90 | d | 1.733 | quint | 2.77, 2.44, 2.40, 1.80, 1.20, (5.59) | 2.44 (8.2), 2.40 (7.70), 2.35 (8), 2.34 (8) |
| 4 | 33.76 | d | 2.354 | | 5.204, (5.593), 2.765, 2.44, 2.40 | 1.73 (8), 2.77 (8), 5.59 (3.5), 5.21 (1) |
| 5 | 127.59 | d | 5.593 | dt | 1.733, 2.765 | 5.21 (10.2), 3.35 (3.5), 2.35 (3.5) |
| 6 | 126.33 | d | 5.207 | dq | 1.851 | 5.59 (10.2), 5.845 (1), 2.35 (1), 3.35 (1) |
| 7 | 34.82 | d | 3.351 | m | 5.20, (5.59), 5.86, 1.85, 1.95 | 5.85 (1), 5.59 (3.5), 5.21 (<1), 4.00 (<1), 2.34 (1), 1.85 (5) |
| 8 | 140.15 | s | — | — | 6.91, 7.00, 5.21, 4.00 | — |
| 9 | 131.41 | d | 5.845 | q | 4.00, (1.95), (1.21) | 3.35 (1), 4.00 (1), 5.21 (1) |
| 10 | 71.96 | d | 4.000 | ddd | 1.21, 1.85, 1.95 | 1.95 (9), 3.35 (<1), 5.85 (1) |
| 11 | 44.02 | d | 1.946 | ddt | 5.85, 4.00, 2.77, 1.21, 1.80, 1.85, 5.59 | 4.00 (9), 1.21 (11.6), 1.80 (4), 1.85 (5) |
| 12 | 34.99 | t | 1.801 1.209 | dd dt | 4.00, 2.76, 1.73 2.34 | 1.21 (11), 1.95 (4) 1.80 (11), 1.95 (11.6), 2.34 (6) |
| 13 | 40.61 | d | 2.339 | | 2.44, 2.40, 1.21, 1.80, 1.73 | 2.77 (8), 1.73 (8), 1.80 (<1), 1.21 (6) |
| 14 | 33.62 | d | 2.765 | q | (5.59), 2.34, 2.35, 1.80, 1.85 | 1.85 (8), 2.35 (8), 2.34 (8) |
| 15 | 40.32 | d | 1.851 | dt | 1.95, 1.80, 5.21, 2.34, (2.77) | 2.77 (8), 3.35 (5), 1.95 (5) |
| 1' | 147.51 | s | — | — | 6.00, 6.87, (7.00) | — |
| 2' | 146.48 | s | — | — | 6.00, 7.00, 6.91, | — |
| 3' | 108.10 | d | 6.873 | d | (7.00) | 6.91 (8.2) |
| 4' | 119.86 | d | 6.908 | dd | 7.00 | 6.87 (8.2), 7.00 (1.6) |

TABLE 1-continued

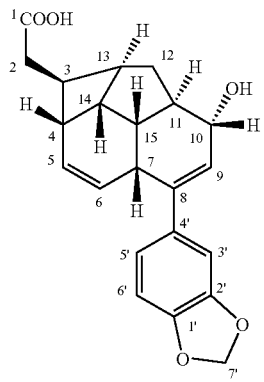

NMR chemical shifts and coupling constants of endiandric acid H, DMSO, 303 K.

| Pos. | δ ($^{13}C$) | m ($^{13}C$) | δ ($^1H$) | m ($^1H$) | $^{nJ}CH$ | $^{nJ}HH^{(J/Hz)}$ |
|---|---|---|---|---|---|---|
| 5' | 133.76 | s | — | — | 6.87, 5.85 | — |
| 6' | 106.66 | d | 6.995 | d | 6.908 | 6.81 (1.6) |
| 7' | 100.92 | t | 6.01 | s | — | — |
|    |        |   | 6.00  | s |   |   |

Example 6

Bioassay

Cell Culture:

A luciferase reporter gene construct (IL-4 luc) was prepared by means of cloning using the human IL-4 promoter (−6635 to +66). The cDNA of full-length murine nuclear factor of activated T cells (N FAT) was cloned into another vector. CHO-K1 cells were then transfected with both vectors (IL-4 luc/NFAT) by electroporation. It was possible to obtain a monoclonal IL-4 luc/NFAT cell line by a G418 selection process. Subsequently, full-length murine c-maf cDNA was cloned into a suitable vector, and the IL-4 luc/NAFT cell line generated was cotransfected therewith. The resulting monoclonal cell line harbors all three vectors (c-maf/IL-4 luc/NFAT) and was used for the screening.

The cells were cultivated in the logarithmic phase of growth at 37° C., 5% $CO_2$ in tissue culture bottles with an area of 225 $cm^2$ in the following medium: Ham's F-12 nutrient mixture supplemented with 10% fetal calf serum, 1% antibiotic/antimycotic, 300 µg/ml Geneticin and 300 µg/ml Zeocin.

Assay Procedure:

16 hours before the assay, CHO-K1 cells were harvested by trypsinization, washed once with PBS without Ca and Mg, resuspended in Ham's F-12 medium which additionally contained 10% fetal calf serum, 1% antibiotic/antimycotic, 0.001% Pluronic, 300 µg/ml Geneticin and 300 µg/ml Zeocin, and then quantified using a hemocytometer. The cells were plated out on microtiter plates in a cell concentration of 2 000 cells per well in 2 µl of medium in each case. The cells are incubated at 37° C. and 5% $CO_2$ overnight.

Stock solutions of the assay substances were dissolved in DMSO. These stock solutions were diluted with Ham's F-12 medium which additionally contained 10% fetal calf serum, 1% antibiotic/antimycotic (Gibco BRL, No. 15240-062), 300 µg/ml Geneticin and 300 µg/ml Zeocin to give various concentrations. The CHO-K1 cells were mixed with 1 µl of the assay substance solutions prepared in this way and then incubated at 37° C. and 5% $CO_2$ for 8 hours. The final concentration of DMSO in this case did not exceed 0.83% per well.

After the incubation time, the cells are in each case mixed with 3 µl of Bright-Glow™ luciferase assay reagent (Promega Corporation, Madison, USA) per well. The plates are then placed in the dark for 30 minutes and subsequently measured in a CyBiTM Lumax reader. DMSO in a final concentration of 33.3% was also assayed as positive control. In addition, the positive controls were standardized to a concentration of 0.83%.

Evaluation:

Each assay plate contains 64 negative controls (wells without added substance) and 64 positive controls (wells in which the cells have been killed with 1 µl of DMSO).

The inhibition was calculated as follows:

$$[1-(LCS_{sample}-LCS_{poscontr})/(LCS_{negcontr}-LCS_{poscontr})]\times 100(\%)$$

Endiandric acid H shows an $IC_{50}$ of 1.5 µM in the bioassay.

What is claimed is:

1. A compound of the formula (I)

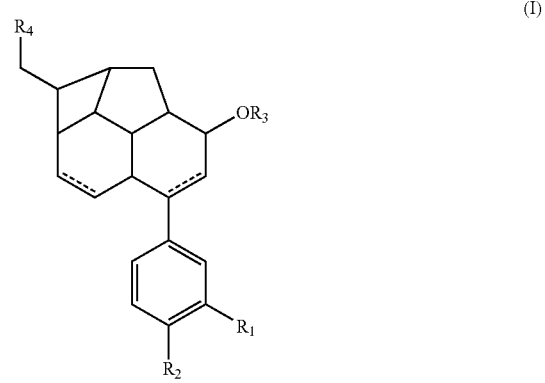

(I)

wherein

R$_1$ and R$_2$ together are —O—CH$_2$—O—,

R$_4$ is

CO$_2$R$_3$, CO$_2$NHR$_3$, CHO, CH$_2$OR$_3$, CH$_2$OSi(R$_3$)$_3$, CH$_2$Br, CH$_2$CN, wherein R$_3$ is, 1.0 H or 2.0 a C$_1$–C$_6$-alkyl, C$_2$–C$_6$-alkenyl, C$_2$–C$_6$-alkynyl or C$_6$–C$_{10}$-aryl group, in which alkyl, alkenyl and alkynyl are straight-chain or branched, and in which the alkyl, alkenyl and alkynyl groups are further mono- or disubstituted by:

2.1 —OH, 2.2 =O, 2.3 —O—C$_1$–C$_6$-alkyl in which alkyl is straight-chain or branched, 2.4 —O—C$_2$–C$_6$-alkenyl in which alkenyl is straight-chain or branched, 2.5 —C$_6$–C$_{10}$-aryl, 2.6 —NH—C$_1$–C$_6$-alkyl in which alkyl is straight-chain or branched, 2.7 —NH—C$_2$–C$_6$-alkenyl in which alkenyl is straight-chain or branched, 2.8 —NH$_2$ or 2.9 halogen, and in which the aryl groups are further mono- or disubstituted by substituents 2.1 or 2.3 to 2.9, in which the substituents 2.3, 2.4, 2.6 and 2.7 are further substituted by —CN, -amide or -oxime functions, and 2.5 are further substituted —CN or amide, or a stereoisomeric form of the compound of the formula (I) or a physiologically tolerated salt of the compound of the formula (I) or a salt of a stereoisomeric form of the compound of the formula (I) provided R4 is not CO2H.

2. The compound according to claim 1, which is the compound of formula (II)

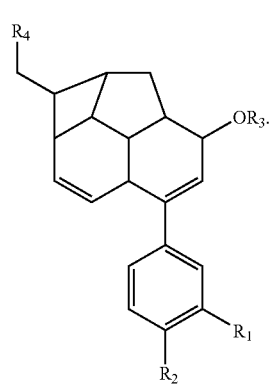

(II)

3. The purified compound isolated from *Beilschmiedia fulva* PLA 101037, which is the compound of formula (III)

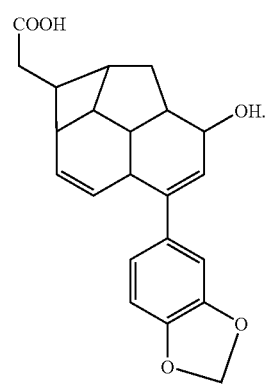

(III)

4. The purified compound according to claim 3, which is the compound of formula (IV)

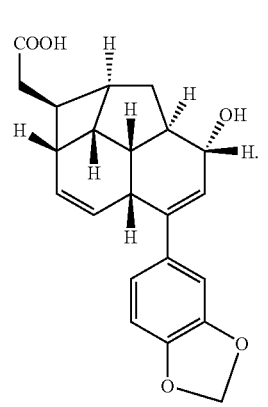

(IV)

5. A process for the preparation of the compound of formula IV, according to claim 4 and each physiological tolerated salt comprising:

1. extracting the plant *Beilschmiedia fulva*, PLA 101037, or cell cultures of the plant *Beilschmiedia fulva*, PLA 101037, under suitable conditions,
2. isolating the compound of the formula (IV),

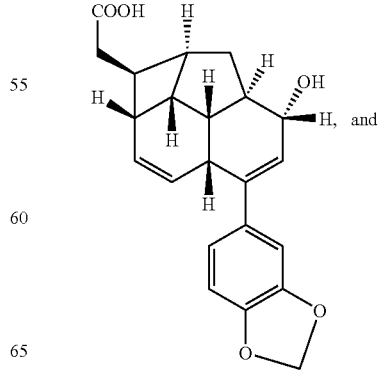

(IV)

3. where appropriate reacting to give physiologically tolerated salt of the compound of the formula (IV).

6. A pharmaceutical composition comprising a compound of claim 1 or a pharmacologically tolerable salt thereof and one or more physiologically acceptable excipients.

7. A process for the preparation of a pharmaceutical composition as claimed in claim 6, comprising bringing a compound of formula (I), or a pharmacologically tolerable salt thereof, into a suitable administration form using one or more physiologically suitable excipients.

8. A method of treating allergies, asthma and inflammation associated with asthma in a patient comprising administering to a patient in need thereof an effective c-maf and NFAT inhibiting amount of a compound according to claim 1.

* * * * *